(12) United States Patent
Johnson

(10) Patent No.: US 7,069,153 B2
(45) Date of Patent: Jun. 27, 2006

(54) CD METROLOGY METHOD

(75) Inventor: Kenneth C. Johnson, Santa Clara, CA (US)

(73) Assignee: Therma-Wave, Inc., Fremont, CA (US)

( * ) Notice: Subject to any disclaimer, the term of this patent is extended or adjusted under 35 U.S.C. 154(b) by 152 days.

(21) Appl. No.: 10/764,792

(22) Filed: Jan. 26, 2004

(65) Prior Publication Data

US 2004/0176928 A1 Sep. 9, 2004

Related U.S. Application Data

(60) Provisional application No. 60/443,028, filed on Jan. 28, 2003.

(51) Int. Cl.
*G01N 21/00* (2006.01)

(52) U.S. Cl. .................. 702/28; 702/127; 702/172; 356/625

(58) Field of Classification Search ............ 702/182, 702/28, 40, 32, 127, 172, 179, 183, 189; 356/237.1–237.5, 600, 601, 625
See application file for complete search history.

(56) References Cited

U.S. PATENT DOCUMENTS

| 5,607,800 | A | 3/1997 | Ziger ........................ 430/8 |
| 5,739,909 | A | 4/1998 | Blayo et al. ............... 356/369 |
| 5,798,837 | A | 8/1998 | Aspnes et al. ............. 356/369 |
| 5,867,276 | A | 2/1999 | McNeil et al. ............. 356/445 |
| 5,889,593 | A | 3/1999 | Bareket .................... 356/445 |
| 5,910,842 | A | 6/1999 | Piwonka-Corle et al. ... 356/369 |
| 5,963,329 | A | 10/1999 | Conrad et al. ............. 356/372 |
| 6,268,916 | B1 | 7/2001 | Lee et al. .................. 356/369 |
| 6,429,943 | B1 | 8/2002 | Opsal et al. ............... 356/625 |
| 6,590,656 | B1 | 7/2003 | Xu et al. ................... 356/369 |
| 6,694,275 | B1 | 2/2004 | Jakadar et al. ............. 702/84 |

(Continued)

FOREIGN PATENT DOCUMENTS

WO    WO 02/27288    4/2002

(Continued)

OTHER PUBLICATIONS

C.J. Raymond, "Scatterometry for Semiconductor Metrology", Handbook of Silicon Semiconductor Metrology, A. Diebold, Ed., New York 2001, Chapter 18, pp. 477-513, no month.

*Primary Examiner*—Hal Wachsman
(74) *Attorney, Agent, or Firm*—Stallman & Pollock LLP

(57) ABSTRACT

A method for rapidly analyzing data gathered during scatterometry and related methods uses a combination of database lookup, database interpolation and theoretical model evaluation. Database lookup is used to provide an initial mapping between a measured optical response and a set of associated measurement parameters. Interpolation is then used to refine the optical response and parameters. A theoretical model is then repeatedly evaluated to refine the optical response and parameters previously refined by the interpolation. In this way, the present invention avoids the inaccuracies associated with traditional interpolation-based analysis and without incurring the computational complexity associated with real-time database supplementation.

18 Claims, 3 Drawing Sheets

U.S. PATENT DOCUMENTS

| | | | |
|---|---|---|---|
| 6,704,661 B1 * | 3/2004 | Opsal et al. | 702/27 |
| 6,768,967 B1 * | 7/2004 | Johnson et al. | 702/179 |
| 6,867,866 B1 * | 3/2005 | Chang et al. | 356/446 |
| 6,898,596 B1 * | 5/2005 | Aikens et al. | 707/6 |
| 6,947,135 B1 | 9/2005 | Johnson | 356/327.2 |
| 2001/0051856 A1 | 12/2001 | Niu et al. | 702/57 |
| 2002/0038196 A1 * | 3/2002 | Johnson et al. | 702/179 |
| 2002/0158193 A1 | 10/2002 | Sezginer et al. | 250/237 |
| 2003/0076511 A1 | 4/2003 | Aikens et al. | 356/636 |
| 2003/0147086 A1 | 8/2003 | Rosencwaig et al. | 356/601 |
| 2003/0204326 A1 | 10/2003 | Opsal et al. | 702/28 |

FOREIGN PATENT DOCUMENTS

| | | |
|---|---|---|
| WO | WO02065545 A2 * | 8/2002 |
| WO | WO 03/009063 | 1/2003 |
| WO | WO 03/054475 | 7/2003 |

\* cited by examiner

CD METROLOGY METHOD

PRIORITY CLAIM

The present application claims priority to U.S. Provisional Patent Application Ser. No. 60/443,028, filed Jan. 28, 2003, the disclosure of which is incorporated in this document by reference.

TECHNICAL FIELD

The subject invention relates to systems used to inspect and analyze semiconductor wafers. In particular, the present invention relates to methods for rapidly evaluating scatterometry data to perform critical dimension and other measurements.

BACKGROUND OF THE INVENTION

As semiconductor geometries continue to shrink, manufacturers have increasingly turned to optical techniques to perform non-destructive inspection and analysis of semiconductor wafers. Techniques of this type, known generally as optical metrology, operate by illuminating a sample with an incident field (typically referred to as a probe beam) and then detecting and analyzing the reflected energy. Ellipsometry and reflectometry are two examples of commonly used optical techniques. For the specific case of ellipsometry, changes in the polarization state of the probe beam are analyzed. Reflectometry is similar, except that changes in intensity are analyzed. Ellipsometry and reflectometry are effective methods for measuring a wide range of attributes including information about thickness, crystallinity, composition and refractive index. The structural details of ellipsometers are more fully described in U.S. Pat. Nos. 5,910, 842 and 5,798,837 both of which are incorporated in this document by reference.

As shown in FIG. 1, a typical ellipsometer or reflectometer includes an illumination source that creates a mono or polychromatic probe beam. The probe beam is focused by one or more lenses to create an illumination spot on the surface of the sample under test. A second lens (or lenses) images the illumination spot (or a portion of the illumination spot) to a detector. The detector captures (or otherwise processes) the received image. A processor analyzes the data collected by the detector. The structural details of ellipsometers are described more fully in U.S. Pat. Nos. 5,910,842 and 5,798,837 both of which are incorporated in this document by reference.

Scatterometry is a specific type of optical metrology that is used when the structural geometry of a sample creates diffraction (optical scattering) of the incoming probe beam. Scatterometry systems analyze diffraction to deduce details of the structures that cause the diffraction to occur. Various optical techniques have been used to perform optical scatterometry. These include broadband spectroscopy (U.S. Pat. Nos. 5,607,800; 5,867,276 and 5,963,329), spectral ellipsometry (U.S. Pat. No. 5,739,909) single-wavelength optical scattering (U.S. Pat. No. 5,889,593), and spectral and single-wavelength beam profile reflectance and beam profile ellipsometry (U.S. Pat. No. 6,429,943). Scatterometry, in these cases generally refers to optical responses in the form of diffraction orders produced by period structures, that is, gratings on the wafer. In addition it may be possible to employ any of these measurement technologies, e.g., single-wavelength laser BPR or BPE, to obtain critical dimension (CD) measurements on non periodic structures, such as isolated lines or isolated vias and mesas. The above cited patents and patent applications, along with PCT Application WO 03/009063, U.S. Application 2002/0158193, U.S. Application 2003/0147086, U.S. Application 2001/0051856 A1, and PCT Application WO 01/97280 are all incorporated herein by reference.

Most scatterometry systems use a modeling approach to transform scatterometry results into critical dimension measurements. For this type of approach, a theoretical model is defined for each physical structure that will be analyzed. The theoretical model predicts the empirical measurements (scatterometry signals) that scatterometry systems would record for the structure. A rigorous coupled wave theory can be used for this calculation. The theoretical results of this calculation are then compared to the measured data (typically in normalized form). To the extent the results do not match, the theoretical model is modified and the theoretical data is calculated once again and compared to the empirical measurements. This process is repeated iteratively until the correspondence between the calculated theoretical data and the empirical measurements reaches an acceptable level of fitness. At this point, the characteristics of the theoretical model and the physical structure should be very similar.

Evaluation of the theoretical models is a complex task, even for relatively simple structures. As the models become more complex (particularly as the profiles of the walls of the features become more complex) the calculations can become extremely time consuming. Even with high-speed processors, real-time evaluation of these calculations can be difficult. Analysis on a real-time basis is very desirable so that manufacturers can immediately determine when a process is not operating correctly. The need is becoming more acute as the industry moves towards integrated metrology solutions wherein the metrology hardware is integrated directly with the process hardware.

A number of approaches have been developed to overcome the calculation bottleneck associated with the analysis of scatterometry results. Many of these approaches have involved techniques for improving calculation throughput, such as parallel processing techniques. An approach of this type is described in a co-pending PCT application WO 03/009063, (incorporated herein by reference) which describes distribution of scatterometry calculations among a group of parallel processors. In the preferred embodiment, the processor configuration includes a master processor and a plurality of slave processors. The master processor handles the control and the comparison functions. The calculation of the response of the theoretical sample to the interaction with the optical probe radiation is distributed by the master processor to itself and the slave processors.

For example, where the data is taken as a function of wavelength, the calculations are distributed as a function of wavelength. Thus, a first slave processor will use Maxwell's equations to determine the expected intensity of light at selected wavelengths scattered from a given theoretical model. The other slave processors will carry out the same calculations at different wavelengths. Assuming there are five processors (one master and four slaves) and fifty wavelengths, each processor will perform ten such calculations per iteration.

Once the calculations are complete, the master processor performs the best fit comparison between each of the calculated intensities and the measured normalized intensities. Based on this fit, the master processor will modify the parameters of the model as discussed above (changing the widths or layer thickness). The master processor will then distribute the calculations for the modified model to the slave processors. This sequence is repeated until a good fit is achieved.

This distributed processing approach can also be used with multiple angle of incidence information. In this situation, the calculations at each of the different angles of incidence can be distributed to the slave processor. Techniques of this type are an effective method for reducing the time required for scatterometry calculations. At the same time, the speedup provided by parallel processing is strictly dependent on the availability (and associated cost) of multiple processors. Amdahl's law also limits the amount of speedup available by parallel processing since serial portions of the program are not improved. At the present time, neither cost nor ultimate speed improvement is a serious limitation for parallel processing techniques. As the complexity of the geometry increases, however it becomes increasingly possible that computational complexity will outstrip the use of parallel techniques alone.

Another approach is to use pre-computed libraries of predicted measurements. This type of approach is discussed in U.S. Pat. No. 6,483,580, (incorporated by reference) as well as the references cited therein. In this approach, the theoretical model is parameterized to allow the characteristics of the physical structure to be varied. The parameters are varied over a predetermined range and the theoretical result for each variation to the physical structure is calculated to define a library of solutions. When the empirical measurements are obtained, the library is searched to find the best fit.

The use of libraries speeds the analysis process by allowing theoretical results to be computed once and reused many times. At the same time, library use does not completely solve the calculation bottleneck. Construction of libraries is time consuming, requiring repeated evaluation of the same time consuming theoretical models. Process changes and other variables may require periodic library modification or replacement at the cost of still more calculations. For these reasons, libraries are expensive (in computational terms) to build and to maintain. Libraries are also necessarily limited in their resolution and can contain only a finite number of theoretical results. As a result, there are many cases where empirical measurements do not have exact library matches.

One approach for dealing with this problem is to generate additional theoretical results in real-time to augment the theoretical results already present in the library. PCT WO 02/27288, published Apr. 4, 2002 suggests a combined approach of this type where a coarse library is augmented by real-time regression. Combined approaches have typically improved accuracy, but slowed the scatterometry process as theoretical models are evaluated in real-time.

Another approach is to use a library as a starting point and generate missing results as needed. For example, U.S. Pat. No. 5,867,276 describes a system of training a library to permit linear estimations of solutions. Alternatively, the use of interpolation is described in U.S. Patent Application 2002/0038196, published Mar. 28, 2002. The use of interpolation avoids the penalty associated with generating results in real-time, but may sacrifice accuracy during the interpolation process. The latter publications are incorporated herein by reference.

For these reasons and others, there is a continuing need for faster methods for computing results for scatterometry systems. The need for faster evaluation methods will almost certainly increase as models become more detailed to more accurately reflect physical structures.

SUMMARY OF THE INVENTION

The present invention provides a method for rapidly evaluating data gathered during scatterometry and related optical metrology procedures. For this method, a theoretical model is used to construct a database for each sample that is to be evaluated. The theoretical model predicts the output (reflected) electromagnetic field that is generated when an incident field is applied to the sample. The relationship between these two fields is referred to in this document as the sample's optical response. The theoretical model is parameterized and each parameter corresponds to a characteristic of the sample such as line width, line profile or layer thickness. The database is a mapping between a series of predetermined parameter sets and their associated optical responses. It is constructed by repeatedly evaluating the theoretical model for each of the predetermined parameter sets and storing the resulting optical responses in association with their corresponding parameter sets.

In general, the database is constructed in an offline, non-realtime basis that precedes the actual measurement of the sample. At the time of measurement, the optical metrology system measures the optical response of the sample. The database is then searched to locate the theoretical optical response and associated parameter set that most closely matches the measured optical response.

An interpolation module is used to refine the results obtained from the database. This refinement is useful because the optical response as measured does not necessarily correspond to any optical response included in the database. To reduce this discrepancy, the interpolation module constructs a series of trial parameter sets. Using an interpolation model, it then constructs an interpolated optical response for each trial parameter set. The process is repeated until an interpolated optical response is computed that closely matches the measured optical response. The calculation that translates each trial parameter set into its associated interpolated optical response ("interpolative refinement") relies only on the database-stored optical responses, without reference to the sample's underlying theoretical model. In this way, the computational complexity of rigorous analysis avoided during the interpolation phase. (The database interpolation method is detailed in U.S. Patent Application 2002/0038196).

A theoretical refinement module is used to refine the results obtained from the interpolation module. This refinement is useful because the optical response generated by the interpolation module may contain errors generated by the interpolation process. As a result, the interpolated optical response does not necessarily correspond to the exact optical response that would be generated by the particular sample being analyzed. To reduce this discrepancy, the theoretical refinement module uses a theoretical model of the sample. Typically, this is the same model that is used to construct the database but it is also possible to use a model that is optimized for runtime performance. The model is repeatedly evaluated using a series of associated parameter sets. Each evaluation produces an optical response that is compared to the measured optical response. This process continues until a desired goodness of fit is achieved. (The refinement may be performed according to the method of PCT application WO 03/009063.)

The parameter set produced by the theoretical refinement module closely matches the actual measurement parameters of the sample. In practice, this level of accuracy may not always be required. For this reason, it is generally desirable to configure the data evaluation method to operate adaptively and use any combination of database search, interpolative refinement and theoretical refinement to produce results having any desired accuracy.

In this way, the present invention avoids the inaccuracies associated with traditional interpolation-based analysis and without incurring the computational complexity associated with real-time database supplementation.

DETAILED DESCRIPTION OF THE PREFERRED EMBODIMENTS

Figure 1:
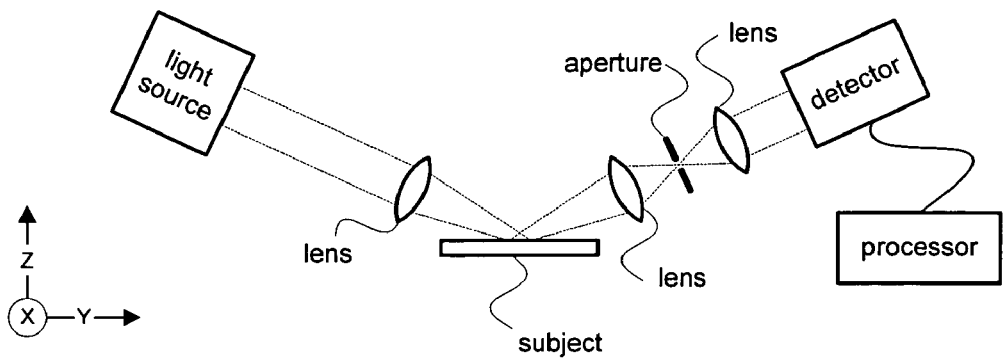
FIG. 1 shows a prior art optical metrology system.
Figure 2:
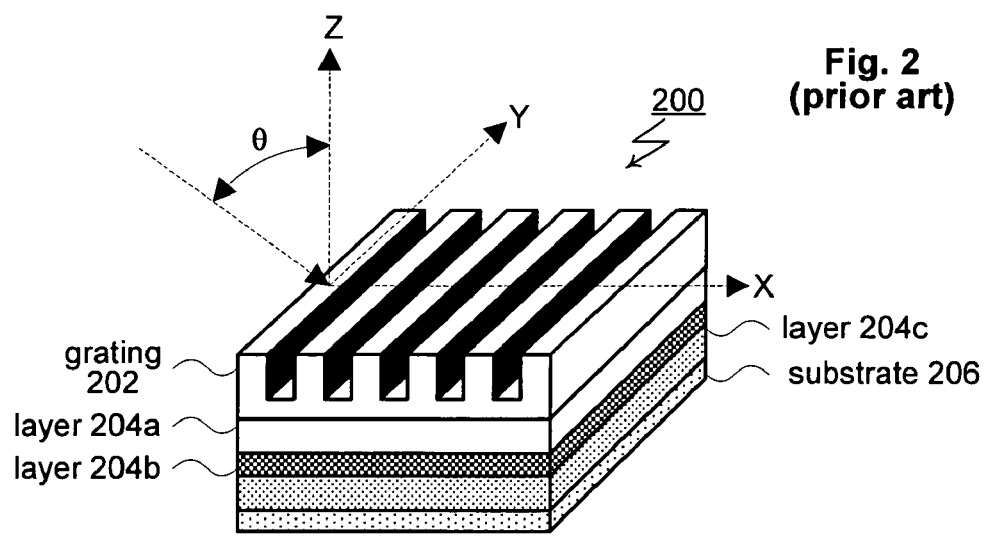
FIG. 2 shows a generic sample suitable for analysis using the present invention.

An aspect of the present invention provides a method for rapidly evaluating data gathered during scatterometry and related optical metrology methods. FIG. 2 shows a generic sample 200 of the type typically analyzed by scatterometry systems. As shown in FIG. 2, sample 200 includes a surface structure 202. For this example, surface structure 202 is a grating that is periodic in the X direction and uniform (exhibits translational symmetry) in the Y direction. In general, the surface structure may be composed of any combination of periodic or isolated, two or three-dimensional structures. Sample 200 is covered by an incident medium (not shown) that is typically air but may be vacuum, gas, liquid, or solid (such as an overlaying layer or layers). Below surface structure 202, sample 200 may include one or more layers constructed using one or more different materials. In FIG. 2, the internal layers are labeled 204a through 204c. At the bottom of internal layers 204, sample 200 includes a final layer, known as a substrate 206.

Optical metrology systems apply an incident field $\psi_{in}$ to sample 200 and measure the resulting output field $\psi_{out}$. By analyzing the output field $\psi_{out}$ optical metrology systems are able to ascertain underlying measurement characteristics about sample 200, such as line sizes and spacings, film properties and thicknesses. The present invention provides a method for rapidly correlating measurements of the output field $\psi_{out}$ to characteristics of this type. Prior to using this method, a library or database is constructed using a parameterized model to represent sample 200. The parameterized model allows a theoretical optical response of sample 200 to be calculated as a function of a set of one or more parameters. Each parameter within the parameter set corresponds to a measurement parameter associated with sample 200 (such as line width, line profile, layer thickness, etc.). The parameterized model is used to build a database. For this task, a series of parameter sets are defined. The theoretical model is evaluated for each parameter set and the resulting optical response is stored (in association with the corresponding parameter set) in the database. The finished database functions as a mapping between the series of parameter sets (measurement characteristics) and their associated optical responses (measurements of the output field $\psi_{out}$).

Figure 3:
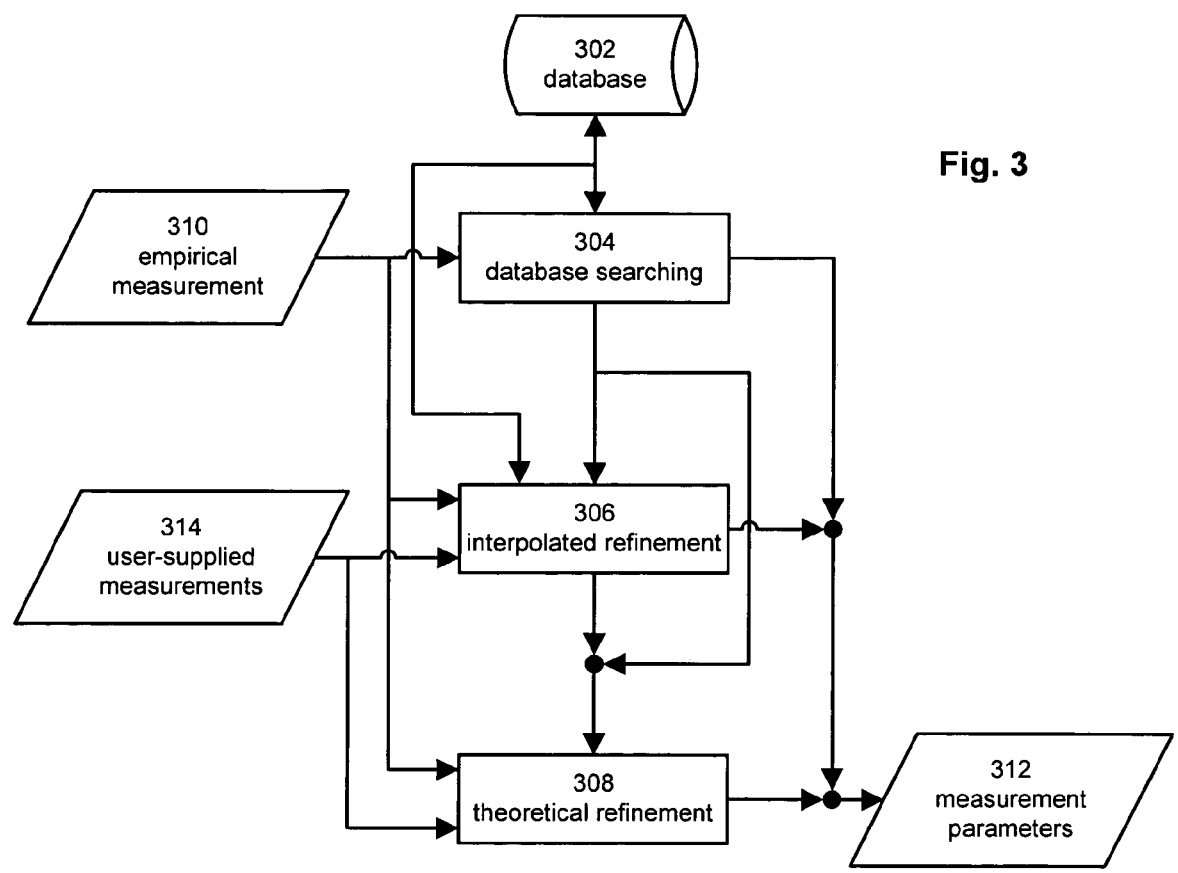
FIG. 3 is a flow diagram showing the modules used by the data analysis of the present invention.
Figure 4:
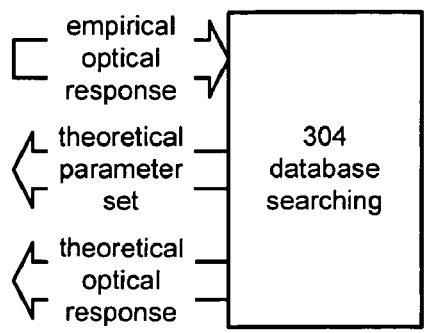
FIG. 4 is a block diagram showing the database searching module used by the present invention.

After the database has been constructed, it becomes one of the runtime components used by the data evaluation method of the present invention. To illustrate, FIG. 3 shows a representative implementation of the data evaluation method including a database 302 (constructed as described), paired with modules for database searching 304, interpolated refinement 306 and theoretical refinement 308. Database searching module 304 performs searching or lookup on database 302. As shown in FIG. 4, database searching module 304 is supplied with an empirical optical response as input. Typically, this consists of one or more empirical measurements obtained during inspection of a sample.

In response, database searching module 304 uses a best-fit strategy to locate the closest matching theoretical optical response within database 302. Database searching module 304 then returns the closest matching theoretical optical response along with its associated parameter set. In this way, database searching module 304 provides a mechanism for mapping measured optical responses to matching parameters sets. The mechanism operates with a degree of built-in granularity and only returns optimal results when a target optical response exactly matches a theoretical optical response that is included in database 302.

Figure 5:
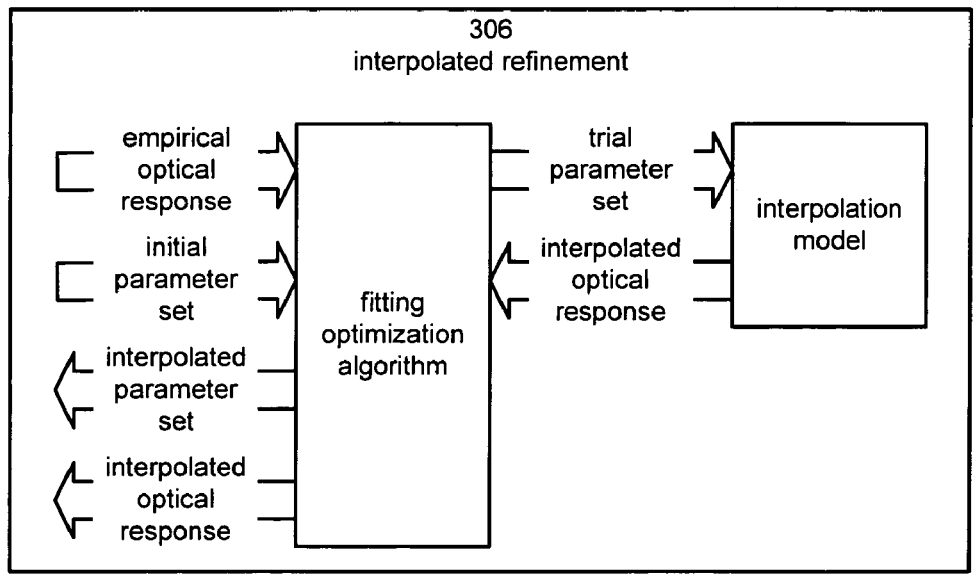
FIG. 5 is a block diagram showing the interpolative refinement module used by the present invention.

Interpolated refinement module 306 is used to enhance the accuracy of results beyond what is available by searching database 302. Interpolated refinement module 306 includes two main components: 1) a fitting optimization algorithm, and 2) an interpolation model. As shown in FIG. 5, the fitting optimization algorithm accepts a target optical response and an initial parameter set as inputs. During the most common use of the data evaluation method, the target optical response and the initial parameter set are the inputs and outputs of database searching module 304 (i.e., the target optical response is obtained during inspection of the sample and the initial parameter set is the corresponding database entry). For other applications, the target optical response and initial parameter set may be user-supplied.

In response, the fitting optimization algorithm generates an interpolated parameter set and an interpolated optical response as outputs. To perform this task, the fitting optimization algorithm starts with the initial parameter set and generates a succession of trial interpolation parameter sets. Each trial parameter set is passed, by the fitting optimization algorithm to the interpolation model for evaluation. The interpolation model calculates a corresponding interpolated optical response for each trial parameter set. The optimization algorithm compares each interpolated optical response to its target optical response. The algorithm selects the trial parameter sets, based on a comparison error minimization method, to iteratively reduce a defined comparison error metric until a defined termination criterion is satisfied. The trial parameters used to achieve the desired goodness of fit (as well as the associated interpolated optical response), are returned as the outputs of the fitting optimization algorithm (and interpolated refinement module 306).

As mentioned, the interpolation model returns an interpolated optical response for each trial parameter set supplied by the fitting optimization algorithm. To perform this task, the interpolation model performs interpolation (or, in some cases extrapolation) using the parameter sets in database 302. This allows the interpolation model to construct interpolated optical responses for trial parameter sets, even for trial parameter sets that are not included in database 302. The construction of interpolated optical responses is performed without reference to the underlying theoretical model. In this way, the interpolation model (and in turn, interpolated refinement module 306) avoids the computational overhead of direct theoretical modeling of sample 200. Various types of interpolation models may be used. In particular, the use of multi-linear or multi-cubic based models is appropriate. Methods of this type are more fully described in U.S. Patent Application 2002/0038196, and U.S. patent application Ser. No. 10/611,298, now U.S. Pat. No. 6,947,135, both of which are incorporated in this document by reference.

Figure 6:
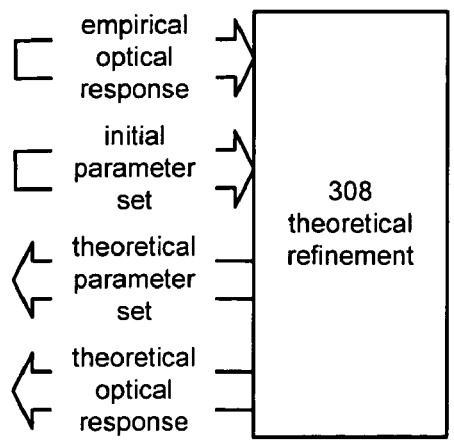
FIG. 6 is a block diagram showing the theoretical refinement module used by the present invention.

Theoretical refinement module 308 is used to enhance the accuracy of results beyond what is available by interpolated refinement module 306. As shown in FIG. 6, theoretical refinement module 308 accepts a target optical response and an initial parameter set as inputs. During the most common use of the data evaluation method, the target optical response is the empirical optical response obtained during inspection of the sample and the initial parameter set is the output of interpolated refinement module 306. For other applications, the target optical response and initial parameter set may be user-supplied. The initial parameter set may also be the output of database searching module 304.

Using these inputs, theoretical refinement module 308 constructs a theoretical parameter set and a theoretical optical response as outputs. To perform this computation, theoretical refinement module 308 uses a theoretical model of sample 200. In most cases, the theoretical model is the same as the parameterized model used to construct database 302. There may, however, be implementations where different models are used for these two applications. As previously described, the theoretical model is parameterized allowing its modeled characteristics to be systematically altered. Using the initial parameter set as a baseline, theoretical refinement module 308 repeatedly evaluates the theoretical model with varying parameters. Each evaluation creates a theoretical optical response. With each repetition, the theoretical refinement module 308 compares this theoretical optical response to the target optical response. The process continues until a desired goodness of fit has been achieved. The parameters used to achieve the desired goodness of fit (as well as the associated theoretical optical response) are returned as the outputs of the fitting optimization algorithm. The theoretical refinement may be performed according to the method of PCT application WO 03/009063, which is incorporated in this document by reference.

The combination of database 302, database searching module 304, interpolated refinement module 306 and theoretical refinement module 308, provide a flexible approach for mapping optical responses to associated measurement parameters. As shown in FIG. 3, a typical application of these components begins with empirical measurements (designated 310 in FIG. 3). Typically, measurements of this type would include optical response information gathered by an optical metrology tool such as a ellipsometer or reflectometer. The empirical measurements would typically be evaluated by initial processing by database searching module 304, followed by refining by interpolated refinement module 306 and theoretical refinement module 308 to produce a set of measurements parameters (designated 312 in FIG. 3). Thus, the typical sequence is empirical measurement followed by database lookup, interpolative refinement and theoretical refinement. Depending on the particular level of accuracy required as well as knowledge about the particular sample 200 involved, any combination of these processes may be bypassed. The particular choice of processes is intended to be dynamically configurable to suit a range of analysis needs. Alternately, the same set of components (in any combination) may be used to analyze user-supplied measurements (e.g., parameter estimates (designated 314 in FIG. 3)).

In this way, the present invention avoids the inaccuracies associated with traditional interpolation-based analysis and without incurring the computational complexity associated with real-time database supplementation.

It should also be noted that the combination of database 302, database searching module 304, interpolated refinement module 306 and theoretical refinement module 308 provide a synergistic benefit that exceeds the simple sum of these separate components. This is because theoretical refinement module 308 reduces the resolution required for database 302. In other words, database 302 may include fewer points sampled at coarser intervals. The use of interpolation, on the other hand, reduces the range of simulations performed by theoretical refinement module 308. This results because the starting value passed to theoretical refinement module 308 is generally closer to the desired result than would be possible without the use of interpolation.

What is claimed is:

1. A method for optically inspecting a sample, the method comprising:
    illuminating the sample with an incident field and obtaining a resulting output field;
    measuring the resulting output field to determine an optical response of the sample;
    generating measurement parameters that correspond to the measured optical response by performing the following operations:
        a) searching a database comprising pre-computed optical responses associated with sets of parameters to locate the one pre-computed optical response that most closely matches the determined optical response,
        b) interpolating, based on the said one pre-computed optical response and the parameter sets in the database, to generate an interpolated optical response that matches the determined optical response within a first defined termination criterion, and
        c) iteratively evaluating a theoretical model to refine the interpolated optical response until the refined interpolated optical response matches the determined optical response within a second defined termination criterion and determining the measurement parameters therefrom.

2. A method as recited in claim 1 that further comprises the step of iteratively evaluating the theoretical model to generate the database.

3. A method as recited in claim 1 wherein the step of interpolating is performed without evaluating the theoretical model.

4. A method as recited in claim 1 wherein the database searching, database interpolation and iterative evaluation operations are performed in sequence to successively refine an optical response and determine the measurement parameters.

5. A method as recited in claim 1 wherein the database interpolation is performed using reduced multicubic interpolation.

6. A method as recited in claim 1 wherein the operations a, b and c are performed in order.

7. A device for optically inspecting a sample, the device comprising:
    a measurement system for illuminating the sample with an incident field and generating a resulting output field, the measurement system operable to measure the resulting output field to determine an optical response of the sample;

a database including sets of sample parameters and associated pre-computed optical responses;

a processor for generating measurement parameters that correspond to the determined optical response, the processor configured to include:

a database searching module for searching the database to locate a pre-computed optical response that best matches the determined optical response;

an interpolated refinement module for interpolating based on the best matched pre-computed optical response and the parameter sets in the database to generate an interpolated optical response that more closely matches the determined optical response; and a theoretical refinement module for iteratively refining the interpolated optical response using a theoretical model and generating the measurement parameters therefrom.

8. A device as recited in claim 7 wherein the database is generated by iteratively evaluating the theoretical model.

9. A device as recited in claim 7 wherein the interpolated refinement module operates without evaluating the theoretical model.

10. A device as recited in claim 7 wherein the database searching module, the interpolation refinement module and the theoretical refinement module are invoked in sequence to successively refine the generation of measurement parameters.

11. A method of evaluating a sample comprising the steps of:

illuminating the sample with an incident field and generating a resulting output field;

measuring the resulting output field to determine a measured optical response of the sample;

searching within a database of pre-computed optical responses and associated sets of measurement parameters to locate the pre-computed optical response that most closely matches the measured optical response;

interpolating to refine the pre-computed optical response located in the database during the searching step and using the parameter sets in the database to more closely match the measured optical response; and iteratively evaluating a theoretical model to refine the optical response obtained by interpolation to more closely match the measured optical response.

12. A method as recited in claim 11 that further comprises the step of iteratively evaluating the theoretical model to generate the database.

13. A method as recited in claim 11 wherein the step of interpolating is performed without evaluating the theoretical model.

14. A method as recited in claim 11 wherein the database interpolation is performed using reduced multicubic interpolation.

15. A method of evaluating a sample comprising the steps of:

creating a database of pre-computed optical responses and corresponding sets of pre-computed measurement parameters of the sample;

optically inspecting the sample to generate an empirical optical response;

comparing the empirical optical response to the pre-computed optical responses stored in the database and selecting the closest match;

using the closest match, interpolating using the parameters sets of the database to generate an interpolated optical response; and; and using the interpolated optical response as a starting point, iteratively evaluating a theoretical model corresponding to the sample to minimize the difference between theoretically generated optical responses and the empirical optical response to produce a best fit for the actual measurement parameters of the sample.

16. A method as recited in claim 15 that further comprises the step of iteratively evaluating the theoretical model to generate the database.

17. A method as recited in claim 15 wherein the interpolated optical response is generated without evaluating the theoretical model.

18. A method as recited in claim 15 wherein the interpolated optical response is generated using reduced multicubic interpolation.

* * * * *